United States Patent
Bartha et al.

[11] Patent Number: 5,527,464
[45] Date of Patent: Jun. 18, 1996

[54] METHOD AND SYSTEM FOR THE TREATMENT AND UTILIZATION OF WASTE PRODUCTS

[76] Inventors: Istvan Bartha, V. Vaci u. 41/a, 1056 Budapest; Sandor Heredy, Erzsebet KU36, 1073 Budapest, both of Hungary

[21] Appl. No.: 350,422

[22] Filed: Dec. 6, 1994

Related U.S. Application Data

[63] Continuation-in-part of Ser. No. 975,288, Nov. 12, 1992, abandoned, which is a continuation-in-part of Ser. No. 901,659, Jun. 19, 1992, abandoned.

[30] Foreign Application Priority Data

Jun. 24, 1991 [HU] Hungary ............ 2251-2091(91)1

[51] Int. Cl.$^6$ ............................................ C02F 3/30
[52] U.S. Cl. .................. 210/603; 210/605; 210/613; 210/630; 71/13
[58] Field of Search ................... 210/603, 605, 210/613, 630, 188, 202, 218, 220, 259, 920, 602; 71/9, 10, 13

[56] References Cited

U.S. PATENT DOCUMENTS

| | | | |
|---|---|---|---|
| 3,579,320 | 5/1971 | Pesses | 71/10 |
| 3,698,881 | 10/1972 | White | 210/602 |
| 4,053,394 | 10/1977 | Fisk | 71/10 |
| 4,185,680 | 1/1980 | Lawson | 71/10 |
| 4,249,929 | 2/1981 | Kneer | 71/9 |
| 4,267,038 | 5/1981 | Thompson | 210/602 |
| 4,501,665 | 2/1985 | Wilhelmson | 210/630 |
| 4,511,370 | 4/1985 | Hunziker et al. | 210/603 |
| 4,692,249 | 9/1987 | Hammel | 210/603 |
| 4,710,300 | 12/1987 | Kristoufek | 71/10 |
| 4,824,571 | 4/1989 | Ducellier et al. | 210/603 |
| 4,846,975 | 7/1989 | Kelyman | 71/10 |
| 5,158,593 | 10/1992 | DeLima | 210/603 |

FOREIGN PATENT DOCUMENTS

| | | |
|---|---|---|
| 178447 | 11/1981 | Hungary . |
| 188016 | 12/1987 | Hungary . |
| 57-209893 | 12/1982 | Japan . |

*Primary Examiner*—Christopher Upton
*Attorney, Agent, or Firm*—Kane, Dalsimer, Sullivan, Kurucz, Levy, Eisele & Richard

[57] ABSTRACT

A method of handling the waste from a community begins with the collection of raw sewage and the separate collection of other bio-degradable solids. The raw sewage is separated into a liquid component and a sludge component. The sludge component of the sewage is combined with the bio-degradable solids in a single bio-mass and adjusted to a relatively dry bio-mass of at least 22–33 percent solids. Fermentated aerobically until a temperature of 60°–65° C. is reached, the ferment is then anaerobically fermentated to produce a high grade manure.

14 Claims, 2 Drawing Sheets

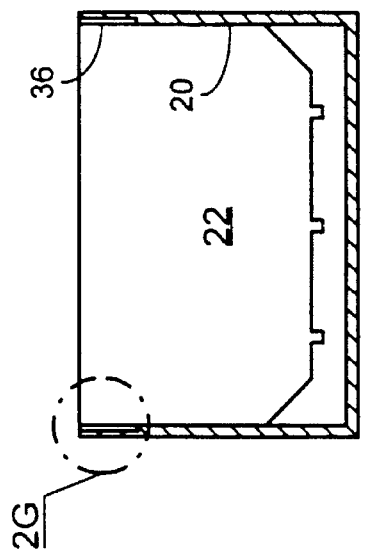
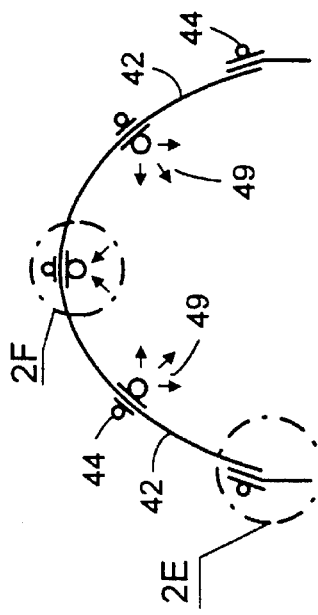
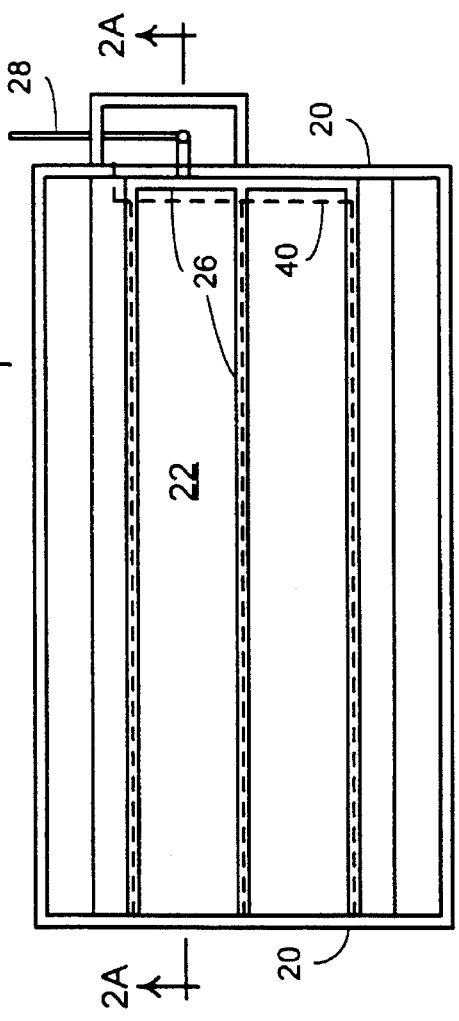
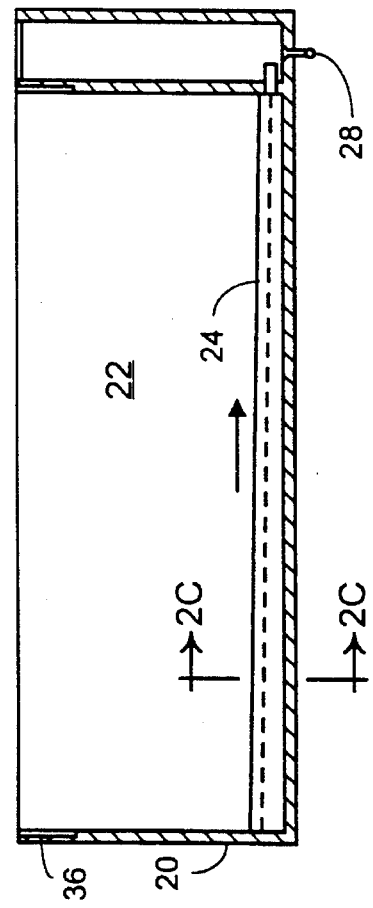

METHOD AND SYSTEM FOR THE TREATMENT AND UTILIZATION OF WASTE PRODUCTS

CROSS-REFERENCES TO RELATED APPLICATIONS

This application is a Continuation-In-Part of my U.S. patent application Ser. No. 07/975,288 filed on Nov. 12, 1992 now abandoned and which was a Continuation-In-Part of U.S. patent application Ser. No. 901,659 filed on Jun. 19, 1992, now abandoned.

BACKGROUND OF THE INVENTION

1. Field of the Invention

The invention relates to a method for the treatment of waste and more particularly makes it possible to solve the problems of waste generated in communities. The environmentally friendly bio-system includes the complete utilization of the treatment products.

2. Brief Description of Related Art

Until now, sewage networks and sewage treatment facilities for several communities have been developed and operated by one specialized company, while the supply of gas to the community has been the business of another specialized company. Waste, both liquid and solid manure, were handled by yet a third company, while agricultural by-products usually are not collected but are dealt with by the large agricultural entities or the small farmers themselves for example, by burning, burial or spreading on fields.

The system of treatment now in use, when the above listed public utilities and transportation of waste are operated independently and without coordination, by several companies and authorities, leads to a large number of environmental problems. Sewage, liquid manure and liquid excrements are transported by carriers or piped to improperly chosen locations and there emptied into the environment. In this manner they do no bring any advantage, rather they are the causes of harm to the environment.

The method of the present invention combines in a single, communal location, a facility for the collection and processing of sewage and bio-degradable wastes into useful agricultural and energy products. The method is so efficient that it meets its own energy requirements and culminates in a positive energy generation instead of consumption. The method can be adapted to any size community, with minimal capital investment. In the method of the invention sewage water, after pre-treatment is utilized in selective irrigation, thus making use of both its water and nutrient value. Sewage sludge and other bio-degradable products are utilized in a centralized treatment plant for the production of bio-gas (processed gas) and bio-manure.

SUMMARY OF THE INVENTION

The invention comprises a method for processing the sewage and other bio-degradable waste collected from a community, which comprises;

receiving the sewage in an aqueous mixture with a solids content of less than about 6 percent;

adjusting the solids content of the sewage to at least about 18 percent by adding bio-degradable waste organic solids, whereby a waste slurry is obtained;

delivering the waste slurry including the bio-degradable waste, as a bio-mass to a single fermentation vessel;

fermenting the delivered bio-mass in the vessel, under aerobic fermentation conditions until the fermentation results in a heating of the bio-mass to a temperature of at least about 60° C., whereby a heated aerobic ferment is obtained;

fermenting the aerobic ferment in the same single fermentation vessel under anaerobic conditions, whereby product bio-gas and bio-manure is generated in the vessel;

separating the product bio-gas from the vessel; and removing the product bio-manure from the vessel.

The method of the invention is essentially a two-step (aerobic and anaerobic) "semi-dry" fermentation of organic waste in one fermentor, sometimes termed a bio-reactor. The fermentation is carried out with the help of bacterium-rich, fluid sewage in a well-defined dry matter/water ratio. The shift in the ratio determines whether the process is "dry", "semi-dry" or "wet". Most of the internationally known, existing treatment plants use "wet" processes. In some processes two separated fermentors (one for aerobic and the other for anaerobic fermentation).

The term "semi-dry" or "dry" as used herein means the fermenting bio-mass contains at least 18 percent solids, and preferably 22 to 30 percent.

The end-products of the bio-chemical processes are bio-gas and bio-manure. The produced gas is, after sufficient compression, useful similar to natural gas in the generation of electricity by gas turbines. The bio-manure, after some adjustment, is a high value fertilizer in agricultures.

Representative of descriptions of the prior art "wet process" i.e., where the waste material is an aqueous mixture with less than about 6 percent solids, is that found in the U.S. Pat. No. 4,511,370 by Hunziker et al. The description is of a process which, in brief, comprises mixing crushed organic matter (particle size circa 1.5 mm) with water to obtain a slurry of 5 to 10 percent solids. The slurry is mixed for about a day under aerobic conditions and then adjusted to a slurry with solids content of 5 to 6 percent. The slurry is then transferred to a fermentation vessel. With heating (through a heat exchanger) the slurry is raised to a temperature of about 60° C., while anaerobic fermentation occurs for a period of 8 days. To assist in maintaining anaerobiosis, methane gas is pumped into the fermenting bio-mass with constant stirring. The gas obtained by the fermentation reaction plus the input methane is collected and leaves a slurry.

In comparison to the wet process of the prior art, the semi-dry process of the present invention has several advantages.

First, the wet process described above requires multiple reaction (fermentation) vessels and transfer of the slurry in and out of each. In contrast, the process of the present invention utilizes a single vessel for aerobic and anaerobic fermentations, with less handling of the bio-mass.

Second, the handling of a bio-mass with a solids content of from 22 to 30 percent solids instead of slurries of 5 to 6 percent results in:

(a) faster heating in the fermentation;

(b) less thermal energy expenditure in the fermentation;

(c) reduced energy expenditure in later removal of water and drying; and (d) handling bio-mass of reduced volume. Smaller fermentation vessels are required (⅕ volume reduction).

Third, less grinding of the material is required. The process of the present invention employing the semi-dry procedure can accommodate organic particulate of average 1–3 cm size. Hunziker, for example, proposes sizes of 1.5 mm, which is energy consumptive. Also, no mixing of shredded organic wastes or other pre-treatment is required. No pre-heating before loading in the fermentor is required.

Fourth, the heat required in the aerobic and anaerobic fermentations is generated by the fermenting bio-mass itself. The bacterial action in the aerobic step, with oxygen, generates the 60° C. to 65° C. plus temperature needed. Hunziker et al's process, as representative of the wet process, uses some 30 percent of the generated bio-gas (methane) for heating subsequent batches of fermenting sludge. The higher percentage of wastes in the bio-mass requires more energy to raise its temperature as seen by the need for a heat-exchanger and strip heaters in the fermentation vessels.

Also, mixing of the bio-mass during anaerobic fermentation, in accordance with the method of the present invention, is not necessary. This is a conservation of energy.

Fifth, the method of the present invention reaches higher fermentation temperatures, for longer periods of time, 25–28 days, thereby providing a greater bio-gas production and sterilization of plant (weed) seeds. The amount of bio-gas available for utilization is 10% higher than with the "wet" process.

Sixth, but not least, the wet process of the prior art produces a compost material which is a liquid slurry, difficult to handle. In contrast, the product of the present invention, without separate drying, produces a stable manure equivalent sterilized material which can be bagged and transported easily as a high value fertilizer. No significant amount of remnant liquid remains to be decanted and conducted back into the sewage system after the fermentation.

BRIEF DESCRIPTION OF THE DRAWINGS

FIG. 2 is a cross-sectional side-elevation of a fermentation vessel for use in the aerobic and anaerobic fermentations carried out according to the invention.

DETAILED DESCRIPTION OF THE PREFERRED EMBODIMENTS OF THE INVENTION

Figure 1:
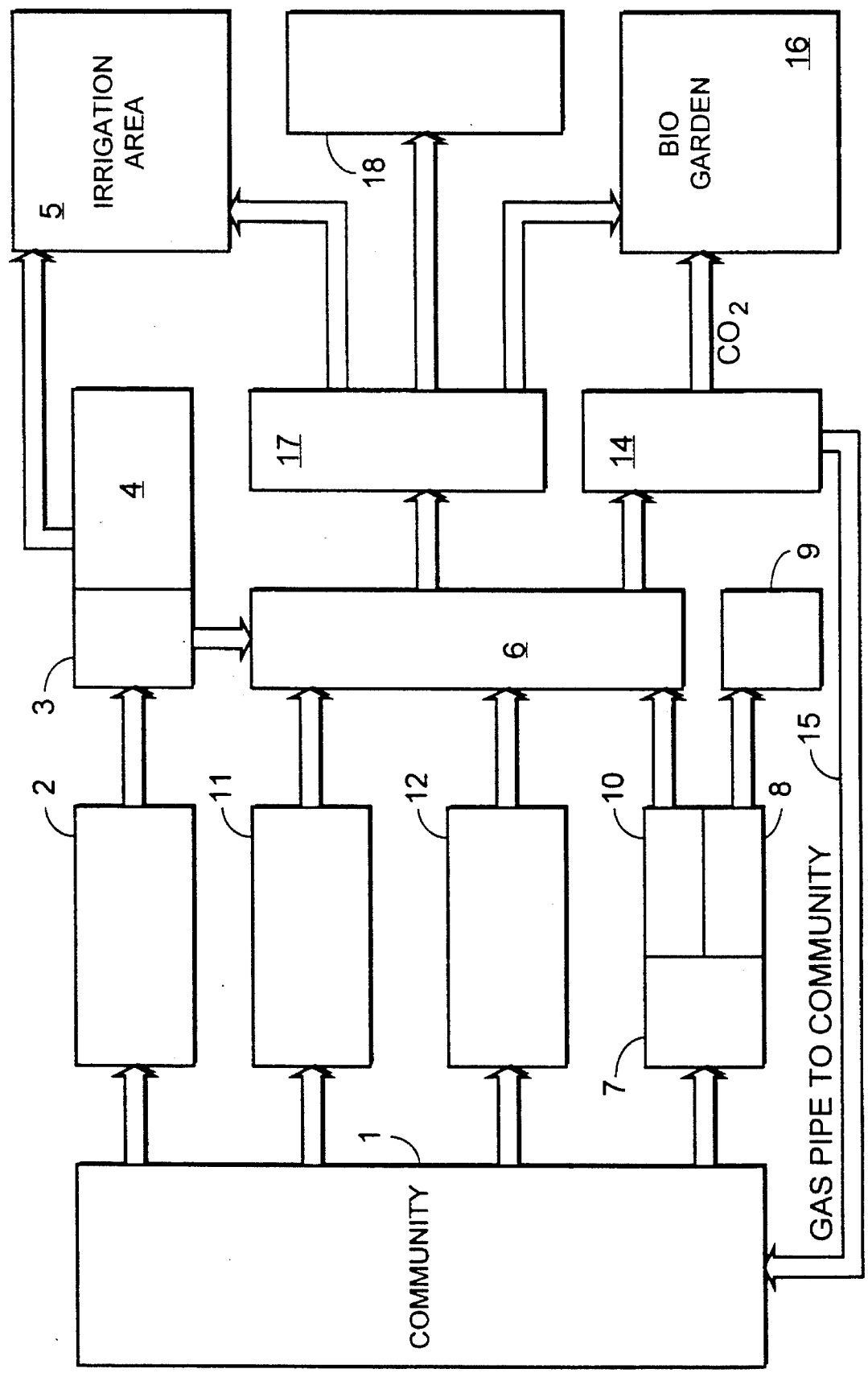
FIG. 1 shows a schematic drawing of the flow handling waste for the community.

With reference to the accompanying drawings, FIG. 1 is a schematic flow chart showing a preferred embodiment process of the invention.

Raw sewage from a community (1) is collected by a pipe network (2) and pumped if necessary through pressurized pipe lines to a location (3) in the process facility. After mechanical pre-treatment and separation waste water is separated and collected in pool (4) and pumped for selective irrigation to area (5). The remaining sewer sludge is pumped to the fermentation section (6). Solid organic wastes with kitchen waste, after selective collection in bio-degradable bags, paper, etc. is transported to the facility section (7). The glass, metal and plastic portion is stored in section (8) and shipped for recycling (9). The organic portion is stored as feed stock in section (10) and transported after shredding for fermentation to section (6).

Farmwaste and plant material waste is stored as feed stock for fermentation, in sections (11) and (12) respectively. From these sections, the waste is transported after shredding for fermentation to section (6).

Bio-gas produced by fermentation in (6) is piped for scrubbing to section (14).

Concentrated (processed) gas obtained from scrubbing is piped back to the community 1 in pipe (15) as fuel.

The $CO_2$ gas resulting from scrubbing is piped to the bio-greenhouse (16) as leaf fertilizer.

Bio-manure left after the fermentation is completed in (6) is stored in section (17) and distributed for use in the bio-garden (16) or by community farm lands and gardens (18). Surplus manure can be sold for other communities.

Thus, the processing plant, in accordance with this invention, is divided into the following sections:

a. sanitary sewer processing section (2), b. solid organic feed stock storage section (10), c. fermentation section (6), with bio-manure storage section (17), d. control and bio-gas processing area (14), e. bio-garden section (16).

The bio-gas processing section is provided with $CO_2$ storage tanks and processed gas storage tanks and the plant is surrounded by a protective wooded barrier and fence. The various facility elements are connected by an appropriate road network and a pipe tunnel network from a control building to the fermentation section (6).

In operation, the organic ingredient of waste generated in a community (i.e. organic waste, kitchen waste collected in bio-degradable bags plus paper products etc.) may be collected in a selective manner to serve as bio-mass input. Glass, metal, and plastic articles separated from the main mass of communal waste by selective collection, are sold as secondary (re-cycled) waste.

In addition, in a farming community, agricultural by-products as well as the liquid and solid manure resulting from animal husbandry, are collected for input into the process of the invention, as bio-mass for the production of bio-gas and/or processed (concentrated) gas and bio-manure.

The bio-mass (solid & liquid) thus collected is used to generate processed-gas for fuel, water for selective irrigating and bio-manure as a source for replenishment of the land with nutrients for agricultural cultivation.

Thus, the facility serves for the utilization of all organic waste generated in the community in such a manner, that the several types of waste serve for the production of materials then utilized, within the community.

One of the advantages of the environmentally friendly utilization of waste according to the invention is the simultaneous concentrated treatment of all types of waste materials.

A further advantage of the facility is, that the community (and/or individual farms) can create an independent company under its own control. The farmer and his employees, or employees of the company, perform the qualified waste treatment in accordance with the technology and utilization of waste deriving from the community, perform maintenance of the sewage network and its renovation, pre-treatment of sewage, its utilization by selective irrigation in co-operation with the agronomic management. Maintenance of the gas distribution network and its surveillance, servicing of gas consumer units, maintenance and repairs of equipment for the production of bio-gas and bio-manure, of the fermentation equipment, collection, storage and disintegration of the bio-mass within the facility. This company may be responsible for the transportation of all the waste and agricultural by-products generated within the community. Lastly, the company can be responsible for the treatment of sewage; the supply of processed-gas; and the utilization of carbon dioxide gas within a greenhouse situated within the confines of the process facility.

In this way the present disorderly and uncoordinated collection and disposal of waste is replaced with a rational, comprehensive, and useful facility for a coordinated system of the above mentioned elements, that takes into account the interaction of several processing technologies.

With realization of the technology proposed in the invention, it is possible to take advantage of the benefits of the elementary technologies of which the system consists, and to utilize the products generated therein. At the same time, the disadvantages of the several fragmented technologies are neutralized by their simultaneous application.

SANITARY SEWER PROCESSING SECTION

Within the sanitary sewer processing section, raw sewage enters the process through pipeline (2) to sewage treatment plant section (3). The sewage may be passed through a bar screen to settling tanks in section (3) for separation into a liquid phase and sewage sludge. The liquid phase is used for selective irrigation of designated community plots and can be stored in waste water storage pool (4). From this pool, it is pumped through pipes to the irrigation area (5). The sewage sludge deriving from settling tanks, may be pumped with grinder pumps through a pipeline to a storage tank prior to delivery as needed to the fermentation section (6).

SOLID ORGANIC FEED STOCK SECTION

The solid waste generated in the community (1) is collected selectively and the organic waste (kitchen waste, yard waste plus paper etc.) is transported to the feedstock storage section (7) of the process facility. Glass, metal, and plastics are collected separately for transportation and sale to a secondary materials collection and utilization section (9) for recycling.

In an agrarian community, liquid and solid animal manure generated by animal husbandry is also transported to the feedstock storage (11) of the process facility. The liquid portion is fed to section (3), while solid portion is fed to section (6). Similarly, all other agricultural, commercial or industrial by-products (straw, corn stalks, food processing, leaves, wood chipping, etc.) generated by the community are also transported to the feedstock storage (12) of the facility.

The materials stored at storage (12) are used as bio-mass for the fermentation section (6), as described below, to provide a year round supply as needed.

FERMENTATION SECTION

Solid, bio-degradable materials from the feedstock storage with the addition of the sewage sludge is adjusted to a solids content of at least 18 percent, preferably 22 to 30 percent, by removal of water. The resulting bio-mass is the bio-mass input of the fermentation center (6). It is provided all year round at regular intervals with various organic materials in accordance with their storage capability, i.e., every three days, one month or six months respectively at the feedstock storage (12). The several types of feedstock are first ground into 1–3 cm. diameter particles and then transported to the fermentation center (6).

At the fermentation center (6) the shredded bio-mass is dumped into one or more fermentation units.

Referring now to FIG. 2, a cross-sectional side elevation, one can see a preferred embodiment fermentation vessel used in the process of the invention.

The fermentation vessel (20) comprises a tub (22) which is advantageously fabricated from concrete. A floor (24) is sloped inwardly to form a drainage channel (26) for draining excess fluids from a contained bio-mass through pipe (28). Around the periphery (30) of the upper wall (32) of tub (22) is a water seal (34) formed by filling the channel (36) with water (38). A plurality of air input nozzles (40) enter the tub (22) near the floor (24) for the injection of compressed air into a contained bio-mass during aerobic fermentation. A flexible, gas-impermeable membrane (42) stretched over a light metal frame (44) covers the entire open top of tub (22). The frame is mounted in the channel (36) so that the water (38) forms a seal with membrane (42) around the entire periphery of the tub (22). In this way, tub (22) is made gas-tight for the containment of bio-gas produced by the contained bio-mass during anaerobic fermentation. The frame (44) together with membrane (42) is removable for access to tub (22) when the vessel is to be charged with bio-mass or emptied of product bio-manure. A gas conduit (48) through the membrane (42) permits separation of generated bio-gas. Temperature sensors, pressure sensors and like instrumentation can be installed in fermentor vessel (20) to monitor the fermentations.

There is a microbiological change during the anaerobic fermentation, lasting for at least 25 days. During this time, pathogenic bacteria, viruses and parasites are reduced at the temperature of 60° C.–65° C. significantly in the first 5 days and below desired limits after 25 days. The germinating ability of weed seeds carried in the bio-mass is reduced by 95–97% and eliminated entirely within 20 days. This result is far better than can be achieved with intermittent manure curing at 60° C. in 5 day's time (Hunziker Process).

The fermentation is the heart of the process of the invention and is performed in two unified stages: aerobic and anaerobic.

The unified two stages or steps are carried out according to a "semi-dry" procedure as defined above. The semi-dry procedure comprises four distinct phases:

1. hydrolysis and liquefication
2. acidogenesis
3. acetogenesis
4. methanogenesis.

The first three phases are driven by aerobic fermentative action of the bacterial of the sewage water, the last phase by the anaerobes during the methanogenesis.

At the hydrolysis phase the non-soluble organic compounds of waste are depolymerized by the hydrolytic exoenzymes of the aerobe bacteria of sewage. There is a high oxygen demand for the process, and during it heat energy will be set free by the chemical bond-splitting. The temperature will be changed from the actual ambient one to circa 60–65 degrees Celsius.

The acidogenesis converts (again by bacterial enzymatic processes) the depolymerized organic compounds to organic, short-chained acids. The oxygen demands remain high, and pH is shifted from 6.0–5.5 down to 4.5–4.0.

In the last phase of aerobic fermentation the organic acids are converted into acetic acid. At the end of this phase the oxygen content of the fermentor is totally exhausted, and temperature is elevated to about 60–65 degrees Celsius. The pH, at this phase, drops from 4.0 to 1.0. In these surroundings the aerobe bacteria are mostly destroyed, but on the other hand, the chemical and physical environment for growth and activity of anaerobe spores and bacteria is very advantageous, and therefore here and now starts the anaerobe phase of methanogenesis.

The bio-gas is produced at the methanogenesis stage. During the gasification the chemical processes are endotherm, and so the temperature drops from about 60–65 degrees Celsius to 30 degrees. At the same time, hydrogen ions are consumed, and the pH is elevated in the alkaline direction.

The produced bio-gas composition is generally about 65% methane, 20–30% carbon dioxide, and the rest is hydrogen with some sulfuric contaminations. In this physico-chemical environment further anaerobe bacterial growth and activity is no longer possible. In this sense the remnant gas/solid products in the fermentor are for all practical purposes "disinfected" by the self-regulating bio-cycles.

The remnant solid product is the bio-manure, whose fertilizing values are determined by the composition of the previously used organic waste. These values can be classified, after chemical analysis, according to the C/N ratio, its nitrogen, phosphate and potassium contents.

After analysis, these contents can be adjusted according to commercial requirement.

Preferably the bio-mass mixture fed into fermentation tubs 3 advantageously has N.P.K. values (nitrogen, phosphate, potassium) in the range of (3–5.4): (2.5–4.4):(0.7–1.9) and the ratio of C/N (carbon-to-nitrogen) is advantageously in the range of 16:1 to 19:1. The dry matter content of the mixture preferably is about 22–30% and it should be in the form of particulate matter wherein the particles do not exceed a particle size of 0.4–1.2 in. (13 cm).

The retention time for the aerobe stage is about one to two days, and for the anaerobe stage is about twenty-eight to twenty-nine days. The loaded mass has optimally 200–500 cubic meters fermentor space. The two-step process may be monitored for temperature, pressure, and pH. The monitoring preferably is continual. It is recommended to check periodically, or by decreasing yields, the used sewage water for heavy metallic salts or for saponine contents, which are mostly industrial contaminants from the sewage system. These compounds interfere with the bacterial enzymatic processes, as enzyme-inhibitors. Such liquid sewage is not desired for fermentation.

In the aerobic stage, air may be pumped with a compressor through pipe (40) and nozzles into the bio-mass in the fermenter (20) to start decomposition. After approximately 60° C., (preferably at least about 65° C.) temperature is reached by the bio-mass, the anaerobic stage is started. Preheated sludge from the sludge collector tank may be pumped into the bio-mass (49), to create the ideal fermentation environment. Generated bio-gas is piped for scrubbing. After fermentation is completed, (approximately 30 days) the bio-manure is unloaded from the fermenter.

CONTROL AND BIO-GAS PRODUCTION

The processing area (14) includes the following:
a. air compressor, to pump air in to fermentation tanks, during the aerobic fermentation process,
b. bio-gas compressor, to raise gas pressure,
c. absorption tower, to separate $CO_2$ gas from bio-gas,
d. solvent pump,
e. desorption tower to separate $CO_2$ gas from solvent,
f. carbon dioxide gas compressor,
g. gas boiler, to heat liquid in tank,
h. control board, to indicate (with remote sensing) various valve settings, temperature, pressure, flow information etc. related to the fermentation process. Remote control valves, pumps, compressors, boiler etc. as required for operation.

The bio-gas from fermentation section (6) is piped to the gas compressor to set required pressure. From the compressor to gas scrubber absorption tower where carbon dioxide gas is separated by solvent. The solvent is pumped into the desorption tower where carbon dioxide gas is separated from solvent. Carbon dioxide gas is compressed and stored in storage tank for ultimate utilization in the bio-garden (16), where it results in a quicker development and increase of efficiency in production of green plants being cultivated. Scrubbed bio-gas or processed (concentrated) gas here after leaving the scrubbing tower is adjusted for heat value and is pressurized to utility standards. Processed gas is stored in a tank and fed to the community through gas pipe (15) and used within the process facility itself. Because of fluctuating gas pressure, a pressure equalizer torch may be provided for security.

The produced bio-gas in the storage tank system can be dried and purified according to the state of the art. Alternatively it can be used for many purposes such as heating without further treatment. Further, the methane and carbon dioxide can be separated according to the well-known chemical ways for electricity generation (methane) through a compressor system and turbines, and the separated $CO_2$, functioning as a feeding component, can be conveyed to the green house/bio-garden attached to the waste-processing plant. (Photosynthesis). A part of the produced electricity can be recycled for the fermenting plants own use, and any remaining amount of energy can supply the adjacent bio-garden or an added pyrolytic plant, processing inorganic and toxic waste.

During the bio-degrading processing, the fermentation tub (22) may be supplied with compressed air from a compressor until temperature of fermented mass reaches a temperature of 60°–65° C. To further the process, a gas tight plastic membrane tent hood, as described above, is placed in position by a crane, after which active bio-gas production and the decomposition of organic matter will commence. A number of fermentation tubs (22) in parallel operation may be used to assure sufficient capacity for the requirement of utilization.

In an alternate embodiment, if the production of bio-gas and bio-manure is in excess of the needs of the community, then to ensure economic operation of the plant, the bio-gas may be used for production of electrical energy for input into the local utility grid, for example, by using an generator. Excess qualities of bio-manure may be offered for sale both on the domestic and the export markets, as its nutrients content (N-P-K) is actually higher than the highest quality of the best processed stable manure, and also its activity has a more prolonged effect.

Obviously numerous modifications may be made to the preferred embodiments of the invention as described above without departing from its scope as defined in the appended claims.

We claim:
1. A method for processing the sewage and other biodegradable waste collected from a community, which comprises;
receiving the sewage in an aqueous mixture with a solids content of less than about 6 percent;

adjusting the solids content of the sewage to at about 22 to 30 percent by adding bio-degradable waste organic solids, whereby a waste slurry is obtained;

delivering the waste slurry including the bio-degradable waste, as a bio-mass to a single fermentation vessel;

fermenting the delivered bio-mass in the vessel, under aerobic fermentation conditions until the fermentation results in a heating of the bio-mass to a temperature of at least about 60° C., whereby a heated aerobic ferment is obtained;

fermenting the aerobic ferment in the same single fermentation vessel under anaerobic conditions, whereby product bio-gas and bio-manure is generated in the vessel;

separating the product bio-gas from the vessel;

separating water from the vessel; and removing the product bio-manure from the vessel.

2. The method of claim 1 wherein the bio-degradable organic solid added has an average particle size of about 1–3 cm.

3. The method of claim 2 wherein the bio-degradable organic solid comprises yard waste and paper.

4. The method of claim 1 wherein compressed air is injected into the bio-mass during aerobic fermentation.

5. The method of claim 1 wherein the anaerobic fermentation is carried out without mixing the bio-mass.

6. The method of claim 1 which further comprises distributing the water separated to irrigate agriculture.

7. The method of claim 1 which further comprises scrubbing the bio-gas product to obtain processed gas similar in heating value to medium pressure natural gas.

8. The method of claim 7 wherein scrubbing removes carbon dioxide from the bio-gas.

9. The method of claim 8 which further comprises delivery of the carbon dioxide to a bio-garden for utilization in growing plant life.

10. The method of claim 7 which further comprises delivery of the scrubbed bio-gas to the community for heating.

11. The method of claim 1 wherein the bio-mass includes solid manure.

12. The method of claim 1 wherein the anaerobic fermentation is carried out for 28 to 30 days at least.

13. The method of claim 1 wherein the aerobic fermentation is carried out for 1 to 2 days.

14. The method of claim 1 wherein the anaerobic fermentation is at a temperature of at least 60°–65° C. until plant seeds in the bio-mass will not germinate.

* * * * *